US009555045B2

(12) United States Patent
Garrigue et al.

(10) Patent No.: US 9,555,045 B2
(45) **Date of Patent: *Jan. 31, 2017**

(54) USE OF PROSTAGLANDINS F2ALPHA AND ANALOGUES FOR THE HEALING OF CORNEAL AND CONJUNCTIVAL LESIONS

(75) Inventors: Jean-Sebastien Garrigue, Verrieres-le-Buisson (FR); Frederic Lallemand, Fresnes (FR); Philippe Daull, Soisy-sur-Seine (FR); Christophe Baudouin, Paris (FR)

(73) Assignee: SANTEN SAS, Evry (FR)

( * ) Notice: Subject to any disclaimer, the term of this patent is extended or adjusted under 35 U.S.C. 154(b) by 490 days.

This patent is subject to a terminal disclaimer.

(21) Appl. No.: 12/950,033

(22) Filed: Nov. 19, 2010

(65) Prior Publication Data

US 2011/0118349 A1 May 19, 2011

Related U.S. Application Data

(60) Provisional application No. 61/262,664, filed on Nov. 19, 2009.

(30) Foreign Application Priority Data

May 28, 2010 (EP) .................................... 10164376

(51) Int. Cl.

| | |
|---|---|
| ***A61K 31/216*** | (2006.01) |
| ***A61K 31/5575*** | (2006.01) |
| ***A61K 9/00*** | (2006.01) |
| ***A61K 9/107*** | (2006.01) |
| ***A61K 45/06*** | (2006.01) |
| ***A61K 47/10*** | (2006.01) |
| ***A61K 47/18*** | (2006.01) |
| ***A61K 47/26*** | (2006.01) |

(52) U.S. Cl.

CPC ......... *A61K 31/5575* (2013.01); *A61K 9/0048* (2013.01); *A61K 9/107* (2013.01); *A61K 45/06* (2013.01); *A61K 47/10* (2013.01); *A61K 47/183* (2013.01); *A61K 47/26* (2013.01); *A61K 31/216* (2013.01)

(58) Field of Classification Search

CPC .......................... A61K 31/216; A61K 31/5575

See application file for complete search history.

(56) References Cited

U.S. PATENT DOCUMENTS 4,599,353 A 7/1986 Bito
4,684,633 A 8/1987 Imagawa et al.
5,321,128 A 6/1994 Stjernschantz et al.
5,496,811 A 3/1996 Aviv et al.
5,510,383 A 4/1996 Bishop et al.
5,588,559 A 12/1996 Vallet Mas et al.
5,688,819 A 11/1997 Woodward et al.
5,767,153 A 6/1998 Bowman et al.
5,830,913 A * 11/1998 Ogawa ................ A61K 31/192 514/569
5,849,792 A 12/1998 Schneider
6,007,826 A 12/1999 Benita et al.
6,011,062 A 1/2000 Schneider et al.
6,225,348 B1 5/2001 Paulsen
6,342,524 B1 1/2002 Hellberg et al.
6,344,477 B1 2/2002 Sharif
7,064,109 B2 6/2006 Luyckx et al.
8,273,362 B2 9/2012 Philips et al.
8,697,751 B2 4/2014 Sakai et al.
2002/0136771 A1 9/2002 Parr et al.
2003/0171438 A1* 9/2003 Ueno .................. A61K 9/0048 514/573
2004/0082660 A1* 4/2004 Ueno ........................... 514/573
2004/0115234 A1 6/2004 Gewirtz
2004/0198829 A1 10/2004 Sponsel et al.
2005/0124699 A1* 6/2005 Akiba et al. ................. 514/573
2008/0268020 A1 10/2008 Philips et al.
2009/0298956 A1 12/2009 Chowhan et al.
2011/0313038 A1 12/2011 Lallemand et al.
2011/0319488 A1 12/2011 Lallemand et al.
2012/0225939 A1 9/2012 Garrigue et al.

FOREIGN PATENT DOCUMENTS

CN 101282714 A 10/2008
CN 101516332 A 8/2009
EP 0423697 A2 4/1991
EP 0696452 A1 2/1996
EP 1532981 A1 5/2005
EP 1547599 A1 6/2005
EP 1655021 A1 5/2006
EP 1681059 A1 7/2006
EP 1972334 A1 9/2008

(Continued)

OTHER PUBLICATIONS

Choi et al., "Low toxicity of cationic lipid-based emulsion for gene transfer", Biomaterials, 2004, pp. 5893-5903, vol. 25.

Database WPI, Section Ch, Week 200377, Derwent Publications Ltd., London, GB; AN 2003-826210, XP002397839 & KR2003046553A, 2003.

Debbasch et al., "Quaternary Ammoniums and Other Preservatives' Contribution in Oxidative Stress and Apoptosis on Chang Conjunctival Cells", Investigative Ophthalmology & Visual Science, Mar. 2001, pp. 642-652, vol. 42, No. 3, Association for Research in Vision and Ophthalmology.

(Continued)

*Primary Examiner* — Zohreh Fay

(74) *Attorney, Agent, or Firm* — Young & Thompson

(57) ABSTRACT

A composition for use in treating corneal and conjunctival lesions, includes a prostaglandin F2alpha or analogue, in a therapeutic amount, the composition being in a form suitable for topical application on the ocular surface and is free of deleterious preservative. A method for treating surface ocular conditions in a patient in need thereof, includes administering an effective amount of the composition.

14 Claims, 10 Drawing Sheets

(56) References Cited

FOREIGN PATENT DOCUMENTS

Figure 1:
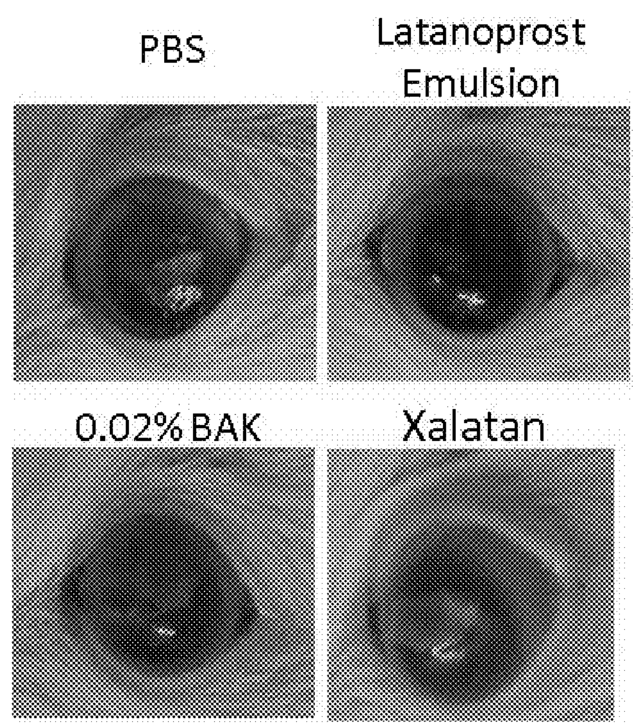

| | | | |
|---|---|---|---|
| EP | 1985298 | A1 | 10/2008 |
| EP | 1994933 | A1 | 11/2008 |
| EP | 2127638 | A1 | 12/2009 |
| KR | 20030046553 | A | 6/2003 |
| MX | 2010012987 | A | 2/2011 |
| WO | 93-18852 | | 9/1993 |
| WO | 03053405 | A1 | 7/2003 |
| WO | 2005044276 | A1 | 5/2005 |
| WO | 2006-050838 | | 5/2006 |
| WO | 2006050836 | A2 | 5/2006 |
| WO | 2007042262 | A2 | 4/2007 |
| WO | 2007-089931 | | 8/2007 |
| WO | 2008-012367 | | 1/2008 |
| WO | 2008036847 | A2 | 3/2008 |
| WO | 2008-074885 | | 6/2008 |
| WO | 2009145356 | A1 | 12/2009 |
| WO | 2010-100218 | | 9/2010 |

OTHER PUBLICATIONS

Furrer et al., "Ocular tolerance of preservatives and alternatives", European Journal of Pharmaceutics and Biopharmaceutics, 2002, pp. 263-280, vol. 53.

Han et al., "Partition of antimicrobial additives in an intravenous emulsion and their effect on emulsion physical stability", Int. J. Pharm., 2005, pp. 263-271, vol. 288.

Jumaa et al., "Physicochemical properties of chitosan-lipid emulsions and their stability during the autoclaving process", International Journal of Pharmaceutics, 1999, pp. 175-184, vol. 183.

Jumaa et al., "A new lipid emulsion formulation with high antimicrobial efficacy using chitosan", European Journal of Pharmaceuticals and Biopharmaceuticals, 2002, pp. 115-123, vol. 53.

Klang et al., "The stability of piroxicam incorporated in a positively-charged submicron emulsion for ocular administration", International Journal of Pharmaceutics, 1996, pp. 33-44, vol. 132.

Klang, et al., "Physicochemical characterization and acute toxicity evaluation of a positively-charged submicron emulsion vehicle", J. Pharm. Pharmacol., 1994, pp. 986-993, vol. 46, abstract.

Klang et al., "Influence of emulsion droplet surface charge on indomethacin ocular tissue distribution", Pharm. Dev. Technol., 2000, pp. 521-532, vol. 5, abstract.

Klang et al., "Evaluatio of a positively charged submicron emulsion of piroxicam on the rabbit corneum healing process following alkali burn", Journal of Controlled Release, 1999, vol. 57, pp. 19-27.

Liu et al., "New cationic lipid formulations for gene transfer", Pharm Res., 1996, vol. 13, No. 12, pp. 1856-1860, abstract.

Nagai et al., "Comparison of Corneal Wound Healing Rates after Instillation of Commercially Available Latanoprost and Travoprost in Rat Debrided Corneal Epithelium", Journal of Oleo Science, 2010, vol. 59, No. 3, pp. 135-141.

Ogawa et al., "Production and Characterization of O/W Emulsions Containing Cationic Droplets Stabilized by Lecithin-Chitosan Membranes", Journal of Agricultural and Food Chemistry, 2003, vol. 51, pp. 2806-2812.

Ott et al., "A cationic sub-micron emulsion (MF59/DOTAP) is an effective delivery system for DNA vaccines", Journal of Controlled Release, 2002, pp. 1-5, vol. 79.

Rabinovich-Guilatt et al., "Extensive surface studies help to analyse zeta potential data: the case of cationic emulsions", Chemistry and Physics of Lipids, 2004, pp. 1-13, vol. 131.

Sznitowska et al., "Physicochemical screening of antimicrobial agents as potential preservatives for submicron emulsions", Eur. J. Pharm. Sci., Jun. 2002, pp. 489-495, vol. 15, No. 5, abstract.

Tamilvanan et al., "The potential of lipid emulsion for ocular delivery of lipophilic drugs", European Journal of Pharmaceutics and Biopharmaceutics, 2004, pp. 357-368, vol. 58.

Tamilvanan et al., "Ocular delivery of cyclosporin A—I. Design and characterization of cyclosporin A-loaded positively-charged submicron emulsion", S.T.P. Pharma Sciences, 2001, pp. 421-426, vol. 11, No. 6.

Varveri et al., "Chemiluminescence monitoring of hemolysis by lysophospholipids", Journal of Photochemistry and Photobiology A: Chemistry, 1995, pp. 121-124, vol. 91.

Washington, C., "Stability of lipid emulsions for drug delivery", Advanced Drug Delivery Reviews, 1996, pp. 131-145, vol. 20.

Zuidam et al., "Chemical hydrolysis of phospholipids", J Pharm Sci., 1995, pp. 1113-1119, vol. 84, No. 9, abstract.

McCarey Bernard et al: "In vivo corneal epithelial permeability following treatment with prostaglandin analoges with or without benzalkonium chloride" Journal of Ocular Pharmacology and Therapeutics, vol. 23, No. 5, Oct. 2007 (Oct. 2007), pp. 445-451, XP002607567.

Baudouin Christophe et al: "In vitro studies of antiglaucomatous prostaglandin analogues: Travoprost With and Without benzalkonium chloride and preserved latanoprost", IOVS, vol. 48, No. 9, Sep. 2007 (Sep. 2007), pp. 4123-4128, XP002607568.

Chung WC et al: "CREB Mediates Prostaglandin F2a-Induced MUC5ACOverexpression", J Immunol. Feb. 15, 2009; 182(4): 2349-2356.

Dilly P N et al: "Surface changes in the anaesthetic conjunctiva in man, with special reference to the production of mucus from a non-goblet-cell source", British Journal of Ophthalmology, 1981, 65, 833-842.

Erb C et al: "German register for glaucoma patients with dry eye. I. Basic outcome with respect to dry eye", Graefes Arch Clin Exp Ophthalmol (2008) 246:1593-1601.

Greiner et al: "Mucus Secretory Vesicles in Conjunctival Epithelial Cells of Wearers of Contact Lenses", Arch Ophthalmol, Oct. 1980, 98, 1843-1846.

Gronert K: "Lipid Autacoids in Inflammation and Injury Responses", Molecular Interventions, Feb. 2008, 8 (1), 28-35.

Landreville S et al: "Expression of Phospholipases A2 and C in Human Corneal Epithelial Cells", Investigative Ophthalmology & Visual Science, Nov. 2004, vol. 45 (11), 3997-4003.

Leung, E W et al:"Prevalence of Ocular Surface Disease in Glaucoma Patients", J Glaucoma 2008;17:350-355.

Mietz H et al:"Latanoprost Stimulates Secretion of Matrix Metalloproteinases in Tenon Fibroblasts Both In Vitro and In Vivo", Invest. Ophthalmol. Vis. Sci. Dec. 2003 vol. 44 No. 12 5182-5188.

Xu W et al:"FP Prostanoid Receptor-Mediated Induction of the Expression of Early Growth Response Factor-1 by Activation of a Ras/Raf/Mitogen-Activated Protein Kinase Signaling Cascade", Molecular Pharmacology Jan. 2008 vol. 73 No. 1 111-118.

European Search Report, dated Oct. 29, 2010, EP 10 16 4376.

Bell, "A new ophthalmic irrigating solution", American Journal of Ophthalmology, Sep. 1951, vol. 34, No. 9, pp. 1321-1322.

Tsukiyama, J., "The effect of prostaglandin derivatives on cornea epithelial wound healing," Japanese Ophthalmological Society, Mar. 2001, vol. 105, pp. 188.

Wilde, "Interfaces: their role in foam and emulsion behaviour", Current Opinion in Colloid & Interface Sciences, Jul. 2000, vol. 5, No. 3-4, pp. 176-181.

* cited by examiner

*, $p<0.05$ when compared to Xalatan® or 0.02% BAK.

USE OF PROSTAGLANDINS F2ALPHA AND ANALOGUES FOR THE HEALING OF CORNEAL AND CONJUNCTIVAL LESIONS

FIELD

The present invention relates to a response/solution for use in the treatment of corneal and conjunctival lesions. Corneal and conjunctival lesions may be due to dry eye syndrome, allergy, injury, cataract surgery, refractive surgery with LASIK or PRK, chemical burn, traumatism, irritation, bacterial, fungal or viral infection or side effects of some medication. A corneal or conjunctival lesion is a local destruction of corneal, conjunctival or goblet cells. Such lesions may be local or disseminated and result in corneal erosion, punctuate keratopathy, epithelial defects, corneal ulceration, corneal scarring, corneal thinning, corneal perforation, corneal oedema, keratitis, conjunctivitis, wounds, tiny abrasions, etc. The composition of the invention is able to improve the healing process of these lesions.

BACKGROUND OF THE INVENTION

Corneal and conjunctival lesions are one of the most diagnosed conditions in patients consulting their physician, and one of the major causes of sight loss. These lesions may be of various origins but are mainly due to allergy, infections (bacterial, viral and fungal), dry eye syndrome, surgery and other traumatisms. These lesions are harmful and very painful. Symptoms of these lesions may be dryness, burning and a sandy-gritty eye irritation. Symptoms may also be described as itchy, scratchy, stingy or tired eyes. Other symptoms are ocular pain, redness, a pulling sensation, and pressure behind the eye. The damage to the eye surface increases discomfort and sensitivity to bright light. Ocular surface lesions need to be treated and healed up very rapidly to avoid worsening of the situation and complications such as ulceration, which may lead to loss of visual acuity and blindness in the most severe cases. For the treatment of lesions due to dry eye syndrome, many lubricating solutions and hydrating hydrogels exist. However, these products only relieve the symptoms but do not accelerate the healing process of the lesions. For deeper lesions, there are some vitamin A solutions, which may help in healing up but with limited efficiency. Beside, compositions enhancing mucins secretion may be of interest. Mucins are extracellular proteins (transmembrane or secreted proteins) which provide protective and lubricating effects to epithelial cells, especially those of cornea and conjunctiva. It has been demonstrated that mucins are secreted by goblet and cornea epithelial cell vesicles and discharged on the surface of the conjuctival epithelium of human eyes (Greiner et. al., Mucus Secretory Vesicles in Conjunctival Epithelial Cells of Wearers of Contact Lenses, Archives of Ophthalmology, 98: 1843-1846 (1980); and Dilly et. al., Surface Changes in the Anaesthetic Conjunctiva in Man, with Special Reference to the Production of Mucus from a Non-Goblet-Cell Source, British Journal of Ophthalmology, 65: 833-842 (1981)).

When addressing the treatment of corneal and conjunctival lesions, an issue is to activate and promote the natural mechanisms of healing such as the cell proliferation and the secretion of growth factors, mucins and glycosyl aminoglycan.

Another issue is to improve/enhance the healing process and to relieve symptoms, associated or not, with dry eye condition.

Xalatan® is, to date, the most prescribed anti-glaucoma medicine in the world. It contains latanoprost, a prostaglandin F2alpha analogue, at a concentration of 0.005%. This product is sold in a multidose bottle of 5 ml preserved by benzalkonium chloride at 0.02%. Even though Xalatan® is very appreciated for the treatment of glaucoma, it has side effects, some of which may be due to the presence of the preservative agent. After a few months of treatment of this chronic life-long disease, Xalatan® eye drops may start to irritate and wound the ocular surface. Thus, people suffering from glaucoma may subsequently suffer from corneal and conjunctival lesions too. Long-term use of this product is also suspected to trigger dry eye condition (Erb et al. 2008; Eamon et Al. J Glaucoma, August 2008). Therefore, the use of preserved medications, including Xalatan®, is not advised for glaucoma patients suffering from ocular surface diseases.

There is an issue for patients having ocular surface conditions, and also suffering from glaucoma, to get an efficient treatment for their glaucoma whereas also treating (and not worsening) their ocular surface lesions or diseases.

US 2005124699 describes the use of topical applications of prostaglandin E for treating or preventing disorders of corneal and/or conjunctival epithelial cells. This patent describes more particularly the use of either prostaglandin E1 or E2, alone, in combination or in combination with an anti-inflammatory drug. Prostaglandins F2alpha are not disclosed nor suggested as a possible treatment for corneal and conjunctival disorders.

Prostaglandins E can be used for the treatment of corneal and conjunctival lesions. However, it is always beneficial for the patient to have alternative treatments in case of allergy or resistance to the treatment.

The Applicant addressed the above-cited technical issues, and formulated a new composition for use in treating corneal and/or conjunctival lesions, wherein the composition comprises a prostaglandin F2alpha analogue or derivative thereof, in a therapeutic amount, preferably in a concentration ranging from 0.0001 to 0.005% w/w of the total composition, said composition being in a form suitable for topical application on the ocular surface and being free of any kind of deleterious preservative.

The composition of the invention was tested in an animal model of ocular surface alteration to evaluate its potential toxicity. As expected, the applicant noticed that the composition of the invention displayed no toxicity sign on the corneal surface, but surprisingly the composition have ocular healing properties. These healing properties are not observed with Xalatan®, even though Xalatan® uses as active agent a prostaglandin (PG) F2 alpha. This is most probably due to the presence of the preservative agent used in Xalatan® that may act as a masking agent for the healing properties of the PG analogue.

The composition of the invention is therefore suitable for the treatment of ocular surface diseases including corneal and conjunctival lesions, more specifically wounds from various origins (surgery, PRK, LASIK, infections, etc.) and dry eye syndrome (from iatrogenic, immunologic or environmental causes).

The composition of the invention has further advantages. For example, prostaglandins F2alpha have been used in ophthalmology for years and their toxicity, side effects and pharmacokinetic profiles are well known. The composition of the invention developed with a prostaglandin F2alpha may be quickly made available to patients thanks to all the knowledge accumulated about these therapeutic agents. As there is an urgent need for a treatment of corneal and conjunctival lesions, the choice of a prostaglandin F2alpha appears appropriate.

Another advantage of the composition is that it may combine various mechanisms of action. In an embodiment of the invention, the composition may be hypoosmotic to correct the effect of dryness. An osmoprotectant such as for example erythritol may be added to the composition to protect corneal cells from osmotic outflow. Thickening and/or moisturizing agents may also be added to exert a lubricating effect and a wetting effect.

In another embodiment, the composition of the invention is isoosmotic.

The prostaglandin may be administered topically either as eye drops or artificial tears; a gel, preferably a viscous gel; a solid insert or an ointment.

The composition may be in the form of a solution, such as for example an aqueous solution, a micellar solution; or in the form of a suspension; or in the form of an anionic or cationic emulsion. According to a preferred embodiment, the composition is a cationic emulsion.

Without willing to be linked by any theory, the Applicant suggests that the effect of prostaglandin F2alpha could be explained according to the following mechanism: prostaglandin F2alpha analogue may activate FP receptor (receptor of prostaglandin F on the cellular surface). This binding may activate secretion of the mucin MUC5AC from the goblet cells, thus increasing the ocular surface hydration and protecting the eye surface (Chung W C, Ryu S H, Sun H, Zeldin D C, Koo J S. CREB mediates prostaglandin F2alpha-induced MUC5AC overexpression. J Immunol. 2009; 182(4):2349-56). The prostaglandin may at the same time increase matrix metalloproteinases (MMP) secretion which favor cell remodelling and cellular shape change during the healing of wounds (Mietz H, Esser J M, Welsandt G, Kociok N, Hueber A, Joussen A, Esser P, Krieglstein G K. Latanoprost stimulates secretion of matrix metalloproteinases in tenon fibroblasts both in vitro and in vivo. Invest Ophthalmol Vis Sci. 2003; 44(12):5182-8.)

The prostaglandin may also improve wound healing via the induction of EGR-1 (early growth response factor-1) (Xu W, Chou C L, Sun H, Fujino H, Chen Q M, Regan J W. FP prostanoid receptor-mediated induction of the expression of early growth response factor-1 by activation of a Ras/Raf/mitogen-activated protein kinase signaling cascade. Mol Pharmacol. 2008; 73(1):111-8.)

The following schemas illustrate the cascade of event consecutive to an exposition to prostaglandin F2alpha: (+) stands for "activation".

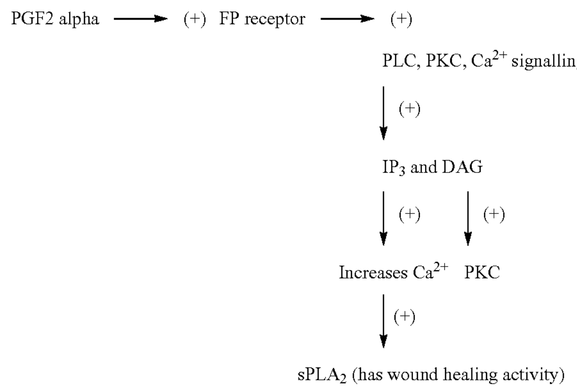

-continued

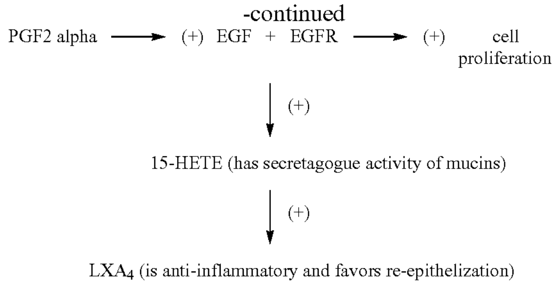

Activation of these cascades may result in the secretion of mucins which contribute significantly to the healing of lesions (Landreville S, Coulombe S, Carrier P, Gelb M H, Guérin S L, Salesse C. Expression of phospholipases A2 and C in human corneal epithelial cells. Invest Ophthalmol Vis Sci. 2004 November; 45(11):3997-4003; Gronert K. Lipid autacoids in inflammation and injury responses: a matter of privilege. Mol Interv. 2008; 8(1):28-35.)

According to the invention, the Applicant selected as active substance a prostaglandin F2alpha or analogue, and derivatives thereof, more preferably latanoprost, acid free latanoprost, 15-keto-latanoprost, latanoprost nitroxide, unoprostone, bimatoprost, travoprost, tafluprost and other derivatives without limitations.

According to an embodiment the concentration of the prostaglandin in the composition is comprised between 0.0001 and 0.005% weight/weight.

According to another embodiment the composition is unpreserved.

According to an embodiment, the composition is stable at room temperature.

According to another embodiment the composition is preserved by soft preservatives. Soft preservatives may be sorbic acid, boric acid, EDTA, zinc sulphate, sodium perborate, purite, or polyhexamethylene biguanide.

The ophthalmic composition may contain antioxidants (ascorbic acid, vitamin E, EDTA).

According to an embodiment, the composition of the invention is sterile. According to a preferred embodiment, the composition of the invention is sterilized by heat or filtration.

According to an embodiment the composition is hypoosmotic.

The composition may be a combination of prostaglandin F2alpha or analogues, and derivatives thereof, with thickening and/or moisturizing agents such as polymers used for the relief of dry eye syndrome such as for example polyvinyl alcohol, dextran, polycarbophil, hydroxypropylmethyl cellulose, carboxymethyl cellulose, polyvinylpyrrolidone, povidone, PEG-400, carbopols, hypromellose, polysorbate 80, hydroxypropyl guar, hyaluronic acid, chitosan, dextran and others without limitation. These polymers may be added alone or with other ones in the composition.

The composition may be combined with osmoprotectants such as for example glycerol, dextrose, propylene glycol, glutamate, choline, N-acetyl aspartate, glycine, betaine, trehalose, proline, L-carnitine, sarcosine, asparagine, glycine, dimethylglycine, taurine, beta-alanine, erythritol, glucose and maltose. The composition may have one or more osmoprotectants.

The composition may also be combined with other healing agents such as for example acetylcysteine, vitamins A, D, E and K, lutein, aloe vera extract such as aloine, cyanocobalamine and derivatives.

The composition may be combined with other agents which may stop infections or activate the epithelial growth factor, i.e. secretagogue agents such as for example 15(S)-HETE, prostaglandins E and F1alpha, or anti-inflammatory agents which may help healing lesions by a mechanism of action complementary to F2alpha prostaglandins. Those agents may be antibiotics such as for example chloramphenicol, ciprofloxacin, gentamycin, erythromycin, vancomycine, imipeneme, sulfadiazine; antifungals such as for example amphotericin B, ketoconazole, econazole, fluconazole, iconazole; antivirals such as for example idoxuridine, acyclovir, ganciclovir, cidofovir, interferon, DDI, AZT, foscarnet, vidarabine; anti-inflammatories such as for example non-steroidal anti-inflammatories such as for example salicylate, indomethacin, ibuprofen, diclofenac, flurbiprofen, piroxicam or steroidal therapeutic agent including but not limited to beclomethasone, betamethasone, corticosterone, cortisone, dexamethasone, dexamethasone palmitate, difluprednate, flumethasone, fluocinolone acetonide, prednisolone, prednisone, rimexolone, tixocortol, triamcinolone and analogues, derivatives, prodrugs, salts and lipophilic esters thereof, prostaglandin E2 derivatives.

In another embodiment, the therapeutic agent may be combined with a healing agent including but not limited to vitamin A, vitamin E, vitamin D and vitamin K, alpha-tocopherol derivatives, retinol derivatives, lutein, aloe vera extracts such as for example aloine, omega-3 fatty acids, cyanocobalamin, L-cystine, pyridoxine, acetylcysteine, essential oils such as for example oil of calendula, cedar, lavender and their analogues and derivatives thereof.

According to an embodiment the composition may be buffered to maintain the pH stable by including appropriate buffers such as for example phosphate or borate buffers.

The composition of the invention may comprise thickening agents and/or moisturizing agents.

According to an embodiment the composition is packaged in single use vials, multidose droppers or preservative-free multidose droppers.

Method of Use

Another object of this invention is a method for treating surface ocular conditions, comprising administration to a patient in need thereof, a composition of the invention as described above, the therapeutic amount of prostaglandin F2 alpha in the composition preferably ranging from 0.0001 to 0.005% in weight to the weight of the total composition. In this embodiment, the composition of the invention is preferably administered at least once per day, with a maximum of four instillations per day.

Another object of this invention is a method for treating surface ocular conditions, preferably corneal and/or conjunctival lesions, comprising administration to a patient in need thereof, a composition of the invention, i.e. a composition comprising a therapeutic amount of a prostaglandin F2alpha or analogue, or derivative thereof. In a preferred embodiment, in the method of the invention, the therapeutic amount of prostaglandin F2alpha or analogue, or derivative thereof in the composition ranges from 0.0001 to 0.005% in weight to the weight of the total composition. Advantageously, the composition used in the method of the invention is free of deleterious preservative. In an embodiment, the prostaglandin F2alpha analogue is selected from the group consisting of latanoprost, acid free latanoprost, 15-keto-latanoprost, latanoprost nitroxide unoprostone, bimatoprost, travoprost, tafluprost. According to an embodiment, the composition is an aqueous solution, a viscous or semi-viscous gel, a suspension, a solid insert or an anionic or cationic emulsion. Preferably, the composition is in the form of eye drops, artificial tears, gel or ointment. The composition used in the method of the invention may be isoosmotic or hypoosmotic. The composition may further comprise osmoprotectants, or other healing agents, buffers, thickening agents, moisturizing agents and antioxidants agents. The composition of the invention, as used in the method, may be unpreserved, preservative-free, self-preserved or preserved with soft preservatives. According to the method of the invention, the composition may be administered at least once per day, with a maximum of four instillations per day. In an embodiment, the composition is administered during three to five days. According to the method of the invention, the composition may further comprise an anti-glaucoma agent, an anti-inflammatory agent, an antibiotic, an antiviral or an antifungal, and other secretagogue compounds.

According to a first embodiment, the patient is not affected by glaucoma. In this embodiment, the therapeutic amount of prostaglandin F2 alpha, preferably latanoprost in the composition of the invention, preferably ranges from 0.0001 to 0.004% or to less than 0.004%, preferably from 0.0005 to 0.002% in weight to the weight of the total composition; in this embodiment, preferably, the composition is administered during three to five days.

According to a second embodiment, the patient is affected by glaucoma. In this embodiment, the therapeutic amount of prostaglandin F2 alpha, preferably latanoprost, in the composition of the invention preferably ranges from 0.004 to 0.005% or from more than 0.004 to less than 0.005% in weight to the weight of the total composition. In this indication, the dose regimen preferably is one drop per day.

Manufacturing Process

Aqueous Solution

Prostaglandin is put at the adequate concentration in water and mixed by magnetic stirring. If the prostaglandin has difficulties to solubilise, the solution may be submitted minutes to a high shear mixer. Also to help the solubilisation, a surfactant or a co-solvent may be added or the solution may be slightly heated to 50° C.

Emulsion

The emulsions of the invention are prepared according to the following steps:

- preparation of the oily phase by mixing the prostaglandin with a saturated oil (such as for example MCT),
- preparation of the aqueous phase by mixing the water-soluble ingredients (osmoprotectant agent, viscosifying agent, buffers) with purified water;
- incorporating the oily phase to the aqueous phase;
- rapidly heating the coarse emulsion obtained, preferably at 75° C.;
- decreasing the emulsion droplet size by any suitable means known to the man skilled in the art, for example by shear mixing;
- cooling down the emulsion preferably to about 20° C. using an ice bath;
- homogenizing the cooled emulsion;
- optionally, adjusting the pH to a physiological pH, by using for example NaOH or HCl;
- optionally sterilizing the emulsion by autoclaving.

DEFINITIONS

In the meaning of this invention, the following terms have the following meanings:

Soft preservatives: a preservative is a compound which keeps the composition free of microorganisms during the period of use. A soft preservative is a preservative which does not have deleterious effects on the ocular surface. It includes: sorbic acid, boric acid, EDTA, zinc sulphate, sodium perborate, purite, or polyhexamethylene biguanide. It excludes benzalkonium chloride, thimerosal, polyquaternium, methyl and propyl parabens, chlorobutanol, cetylpyridinium chloride, benzododecinium bromide used at usual concentration.

Deleterious preservatives are preservatives which damage the ocular surface after one to multiple applications or act as a masking agent preventing the prostaglandine from healing corneal and conjunctival lesions. They include benzalkonium chloride, thimerosal, polyquaternium, methyl and propyl parabens, chlorobutanol, cetylpyridinium chloride, benzododecinium bromide used at usual concentration i.e. at concentration ranging from 0.006% and 0.2%.

Therapeutic amount means an amount or concentration of active substance sufficient to produce a therapeutic effect on an ocular condition so as to reduce or prevent a symptom of said ocular condition, as compared to an untreated eye.

Multidose preservative-free bottle is a multidose container which system allows avoiding the use of preservatives to maintain sterility.

Osmoprotectants: Osmoprotectants are compounds which prevent cell's bursting or plasmolysis when submitted to an osmotic shock by penetrating in the cells and regulating the osmotic flux. These compounds include: glycerol, dextrose, propylene glycol, glutamate, choline, N-acetyl aspartate, glycine, betaine, trehalose, proline, L-carnitine, sarcosine, asparagine, glycine, dimethylglycine, taurine, beta-alanine, erythritol, glucose and maltose.

Corneal and conjunctival lesions: are defined as any damage, wound, injury or irritation of the corneal and conjunctival cells/tissue caused by allergy, dry eye syndrome from iatrogenic, immunologic or environmental causes, chemical burn, infection from viral, bacterial or fungal origin, injury or surgery (PRK, LASIK) or other physical and chemical injury or traumatism.

Unpreserved is said for eye drops not passing the European and US pharmacopeia antimicrobial efficacy tests. According to an embodiment, an unpreserved composition is free of any preservative.

Pharmaceutically acceptable carrier refers to any vehicle which when formulated, is safe and provides appropriate delivery to the ocular surface of an effective amount of prostaglandin F2alpha.

Prostaglandin F2alpha or Prostaglandin F2alpha analogues: A prostaglandin is a member of a group of lipid compounds that are enzymatically derived from fatty acids and have important functions in the body. Every prostaglandin F2alpha contains 20 carbon atoms, including a 5-carbon ring. They are mediators and have a variety of strong physiological effects. There are many different families of prostaglandins, each being specific of a particular receptor creating a particular effect. Prostaglandin F2alpha and analogues bind to the prostaglandin F2alpha receptor. The analogues may represent the different isoforms such as for example 5-6 trans, 15-keto, 15-epi, 15(S) prostaglandin F2a, modified prostaglandin such as for example esters, ethers, amides, nitroxide, peptydyl such as for example latanoprost, travoprost unoprostone, bimatoprost and others.

Healing agent is a compound, which initiates, promotes, improves, enhances or contributes to the natural healing process of lesions in the human body. They include acetylcysteine, vitamins A, D, E and K, lutein, aloe vera extract such as for example aloine, cyanocobalamine.

Buffers are compounds, which maintain the pH of the composition at a defined value: they may include phosphate, acetate, citrate, carbonate or borate buffers or a combination thereof.

Thickening agents and/or moisturizing agents are compounds that are used to relieve dry eye syndrome. They may include polyvinyl alcohol, dextran, polycarbophil, hydroxypropylmethyl cellulose, carboxymethyl cellulose, polyvinylpyrrolidone, povidone, PEG-400, carbopols, hypromellose, polysorbate 80, hydroxypropyl guar, hyaluronic acid, chitosan, dextran, and others without limitation, or a combination thereof.

Antioxidants are compounds that prevent or delay deterioration of products by the oxygen present in the air. They may include vitamin C, vitamin E, EDTA, sodium bisulfite or a combination thereof.

Secretagogue compounds are a substance that causes another substance to be secreted in a controlled manner such as for example prostaglandins E, which promote the secretion of mucins.

BRIEF DESCRIPTION OF THE DRAWINGS/FIGURES

FIG. 1. Ocular surface scars at day 4 post corneal deshepithelization in the rat.

Figure 2:
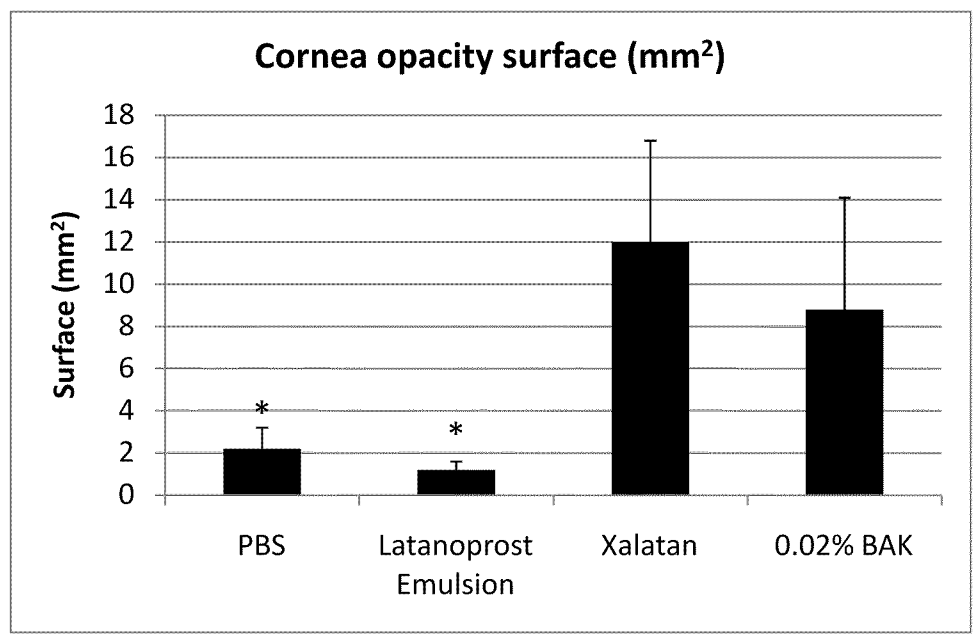

FIG. 2. Corneal scar area measured at the end of the treatment period. *, $p<0.05$ when compared to Xalatan® or 0.02% BAK.

Figure 3:
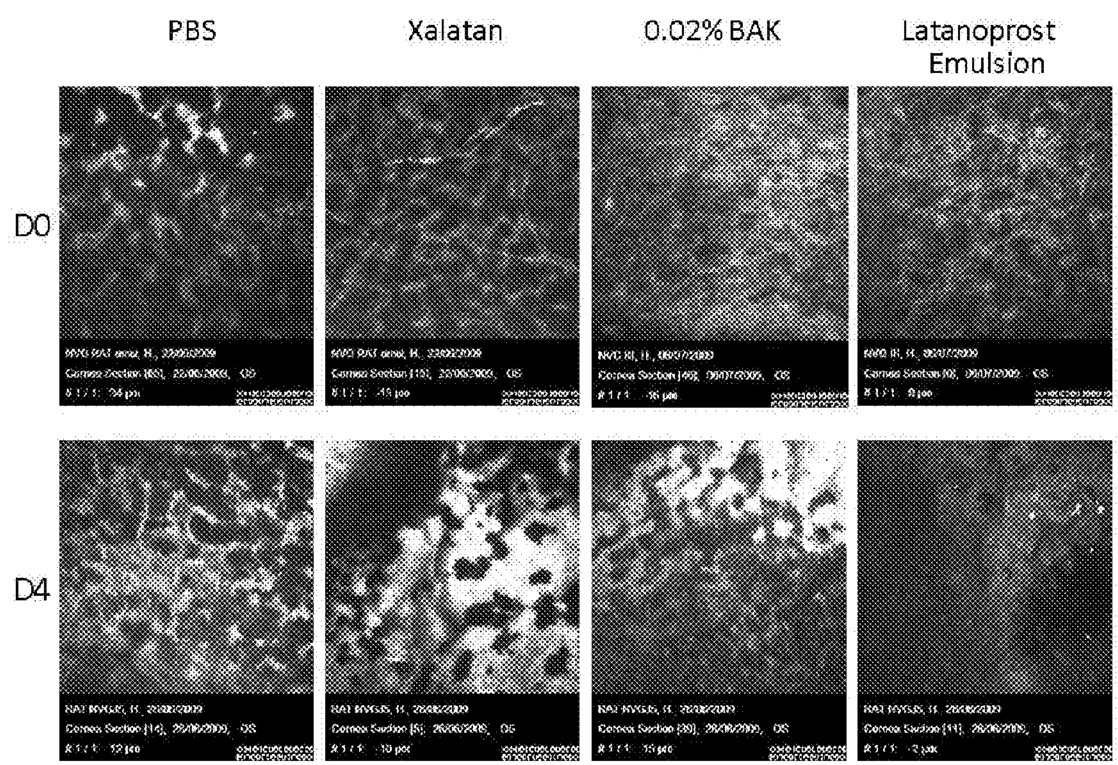

FIG. 3. In vitro confocal microscopy imaging of the superfical epithelium of the treated ocular surfaces at day 4, and compared to day 0 basal conditions.

Figure 4:
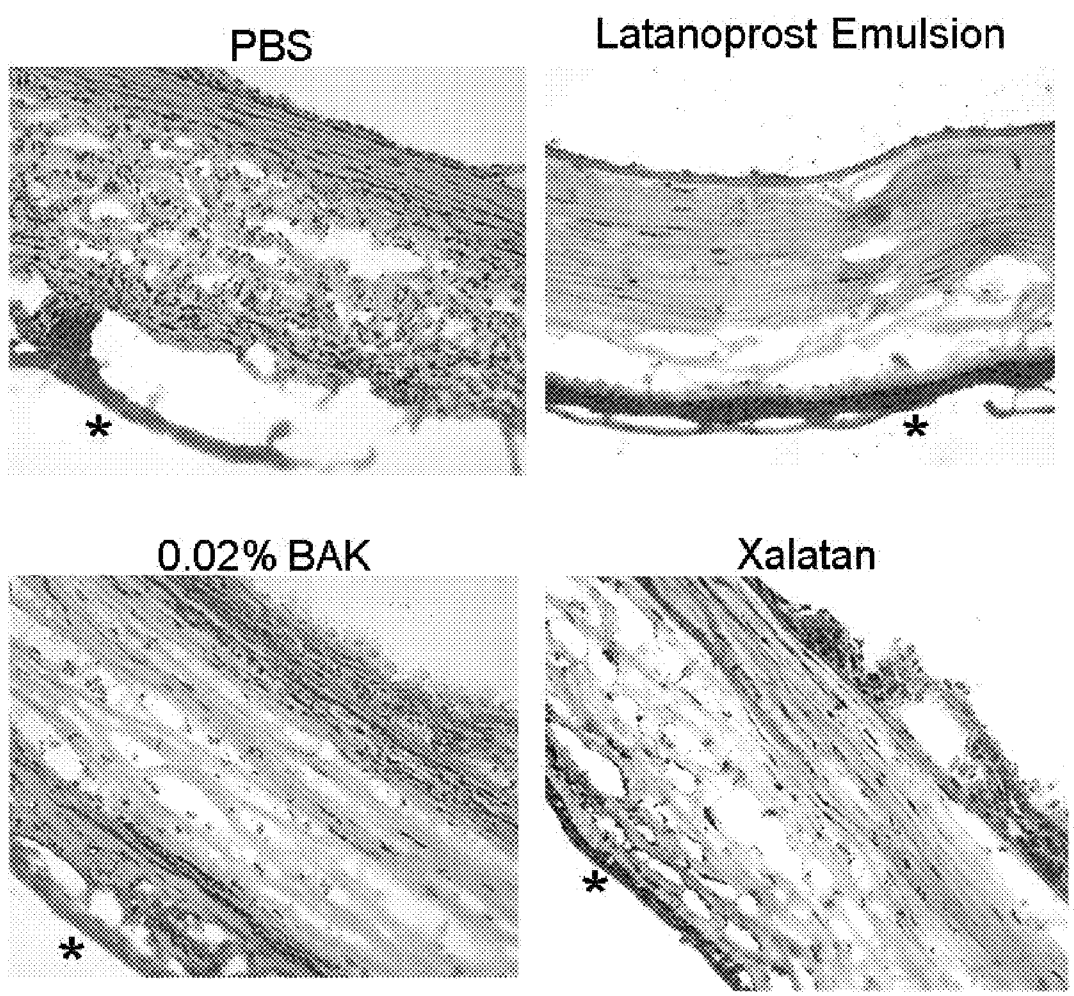

FIG. 4. Hematoxylin-eosin staining of the treated rat corneas. The * locates the epithelium on the cornea.

Figure 5:
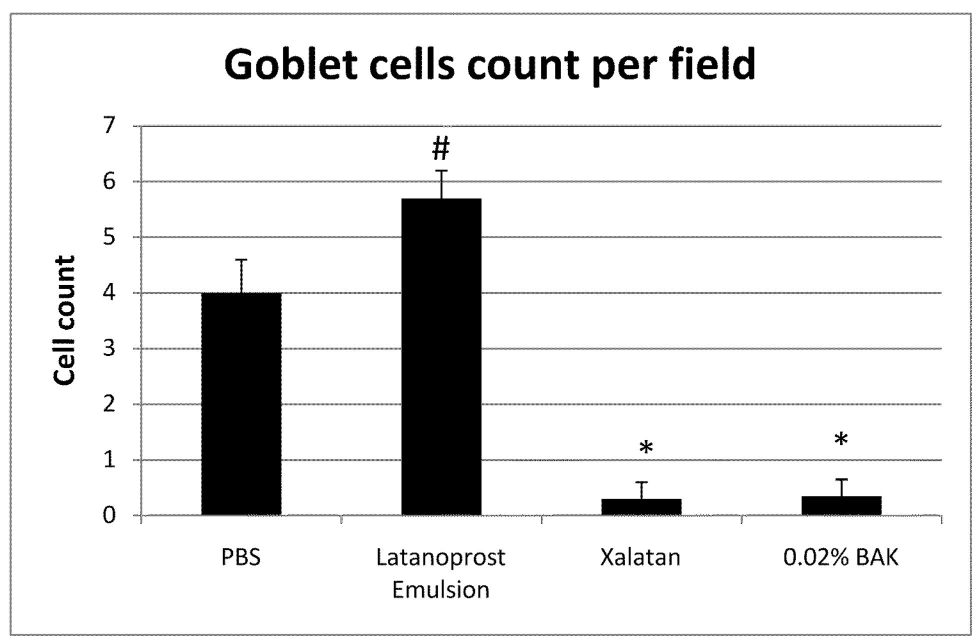

FIG. 5. Goblet cells count in the conjunctiva at the end of the experimental period. #, $p<0.02$ when compared to PBS; *, $p<0.0001$ when compared to PBS or to the Latanoprost Emulsion of the invention.

Figure 6:
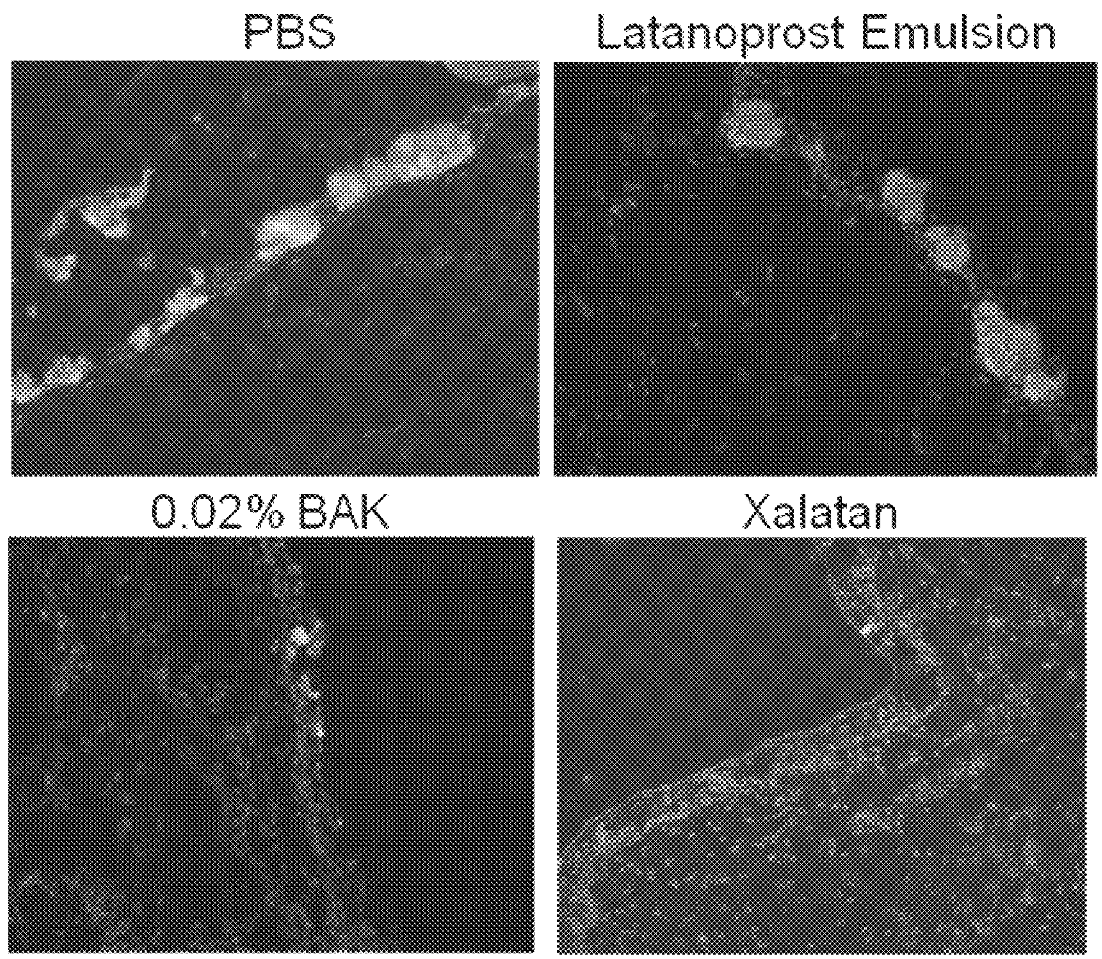

FIG. 6. MUC5AC immunohistological localization on the conjunctiva of treated eyes.

Figure 7:
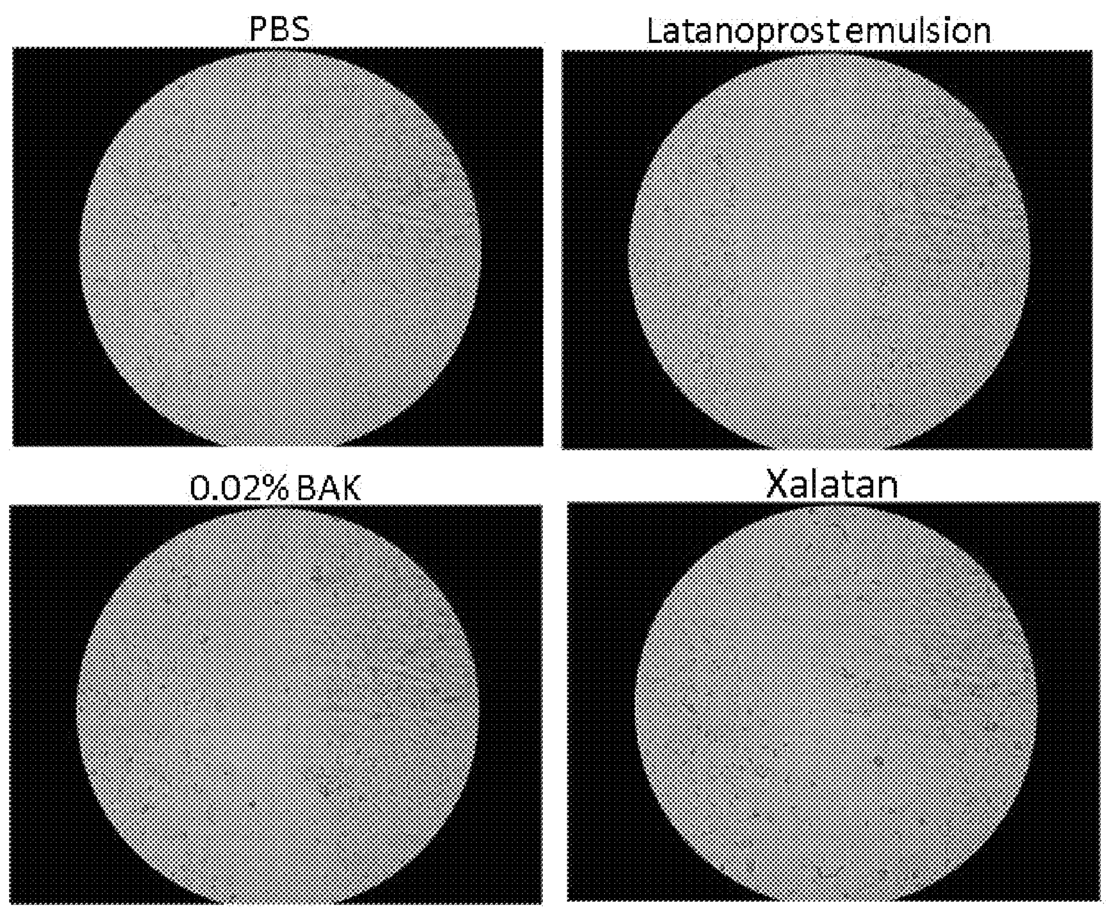

FIG. 7. Efficacy of the different treatment on cell survival and migration 2 hours post scraping and eye drop challenge.

Figure 8:
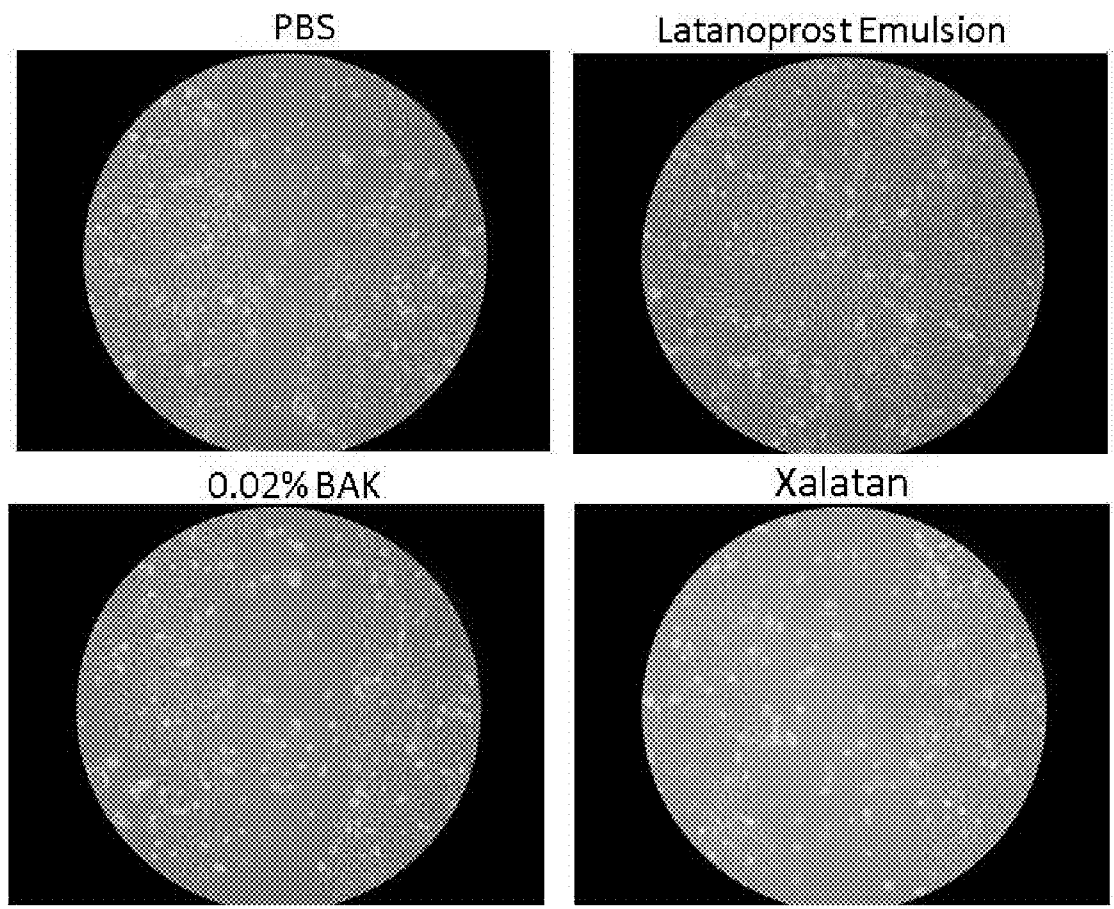

FIG. 8. Efficacy of the different treatment on cell survival and migration 24 hours post scraping and eye drop challenge.

Figure 9:
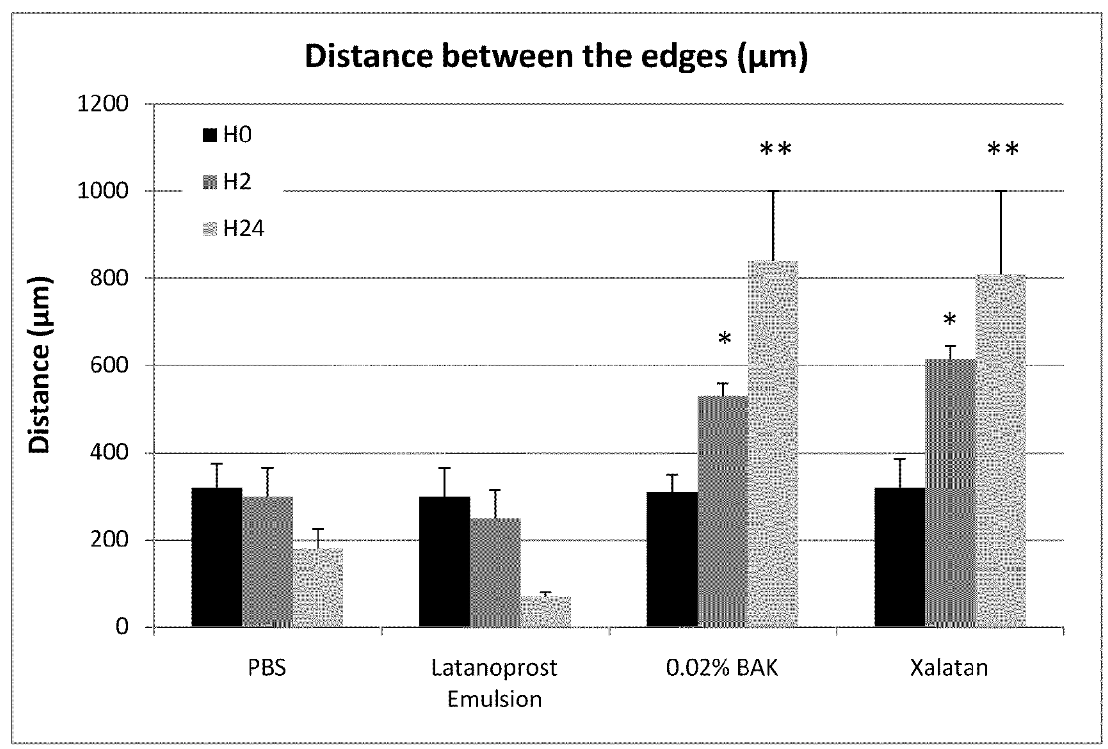

FIG. 9. Wound closure at 2 and 24 hours post scraping measured as the distance between the edge of the monocellular layer. *, $p<0.01$ when compared to PBS or to the Latanoprost Emulsion of the invention; **, $p<0.002$ when compared to PBS or to the Latanoprost Emulsion of the invention.

Figure 10:
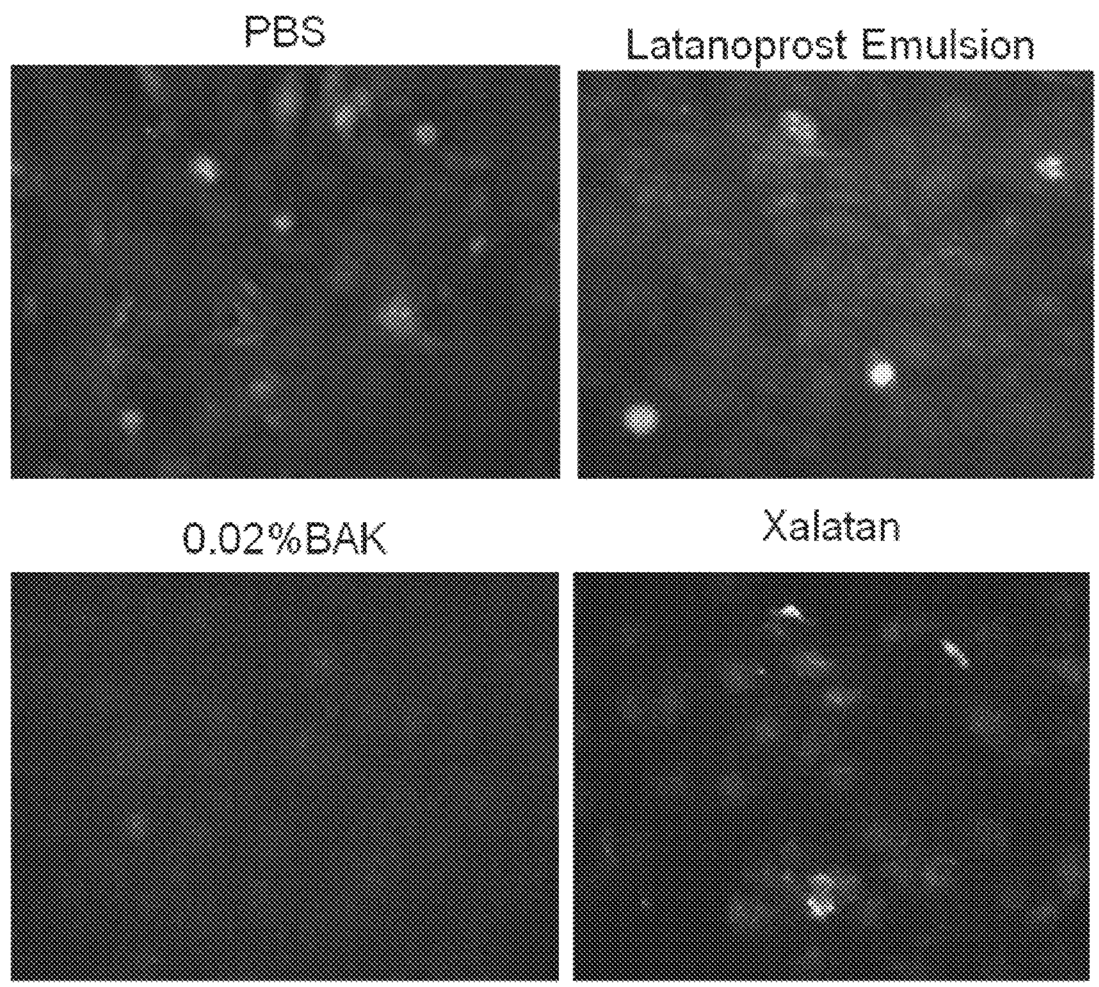

FIG. 10. Ki67 immunohistological identification of the treated cells. Note that the dividing cells appear in gray to white on the pictures.

EXAMPLES

Example 1

In Vivo Experiments

Brief description of the protocol: 16 male Sprague-Dawley rats weighting 100 to 125 g were randomly assigned to 4 groups (4 rats per group (Gp)): Gp1, Phosphate buffer solution (PBS); Gp2, 0.02% benzalkonium chloride (BAK); Gp3, Xalatan®; Gp4, Latanoprost Emulsion. Following general and local anesthesia with ketamine/xylazine and topical Oxybucaïne, respectively, the upper part of the right eye cornea of each rat was scraped with a surgical scalpel following an application of 50 μl of 50% ethanol solution. The upper corneal and limbal epithelia were removed (at day D0). One drop of Tobrex was instilled immediately after the scraping. 2 and 5 hours post scraping one drop of the different test articles were applied onto the cornea of the right eye. These latter instillations were repeated every day for 4 days, and corneal evaluation with an in vivo confocal microscope (IVCM-HRT) was performed on day 4 after the last instillation. At the end of the experimental procedure (the total duration of the treatment is 5 days; from day D0 to D4), the animals were sacrificed and the eyes harvested to characterize the histological organisation of the treated cornea. The conjunctival integrity and functionality were evaluated by the assessment of goblet cell counts, and the immunohistological characterization of MUC5AC secretion profile, respectively.

Results: Day 4 corneal opacity demonstrated that scarification of the cornea was dramatic following repeated instillations with either Xalatan® or a 0.02% BAK solution. By opposition, the Latanoprost Emulsion of the invention favours corneal healing without these sight-threatening scars. FIG. 1 presents pictures of treated cornea at day 4 following scraping and repeated instillations of the different test articles. Clearly, the Latanoprost Emulsion of the invention favors a safe corneal wound healing, as very little white scar tissue is present onto the cornea.

The surface of this white area was measured at day 4 for each of the treated eyes (see FIG. 2). Clearly, the Latanoprost Emulsion of the invention presents a very nice healing profile when compared to Xalatan®. Moreover, the Latanoprost Emulsion of the invention has an improved efficacy over PBS.

IVCM (in vivo confocal microscopy) data confirmed that the cornea was indeed very well healed, without the formation of scars tissue (the white areas seen on the pictures of FIG. 3). Note that the scar tissue (hypereflectivity) seen in the pictures obtained at day 4 for Xalatan® and the 0.02% BAK solution is the result of corneal edema and tissue disorganisation, thus clearly indicating the toxicity of both test items. By opposition, the absence of this hypereflectivity in eyes treated with the Latanoprost Emulsion of the invention demonstrates the beneficial effect of the prostaglandin analogue, as even the PBS control presents a slight oedema (i.e. the diffuse white regions between the cells). It is noteworthy, that the potential healing effect of latanoprost was masked and prevented by the presence of BAK (0.02%), since the prostaglandin analogue present in Xalatan® was unable to protect the corneal epithelium and stroma from the deleterious effect of the conservative agent.

The hematoxylin-eosin staining of the treated cornea confirmed the positive effect of the Latanoprost Emulsion of the invention. Neither epithelium thinning, nor major stroma infiltrations with important inflammatory infiltrates were observed in the cornea of rats treated with the said Latanoprost Emulsion of the invention (see FIG. 4). The edemas and inflammatory infiltrates are particularly obvious in the 0.02% BAK- and Xalatan®-treated animals. The Latanoprost Emulsion of the invention is clearly associated with an improvement of the corneal healing process and the preservation of corneal integrity.

From a functional point of view, the Latanoprost Emulsion of the invention possesses also beneficial effects when compared to PBS- (control), Xalatan®- and 0.02% BAK-treated eyes. The conjunctival goblet cells are preserved (FIG. 5), as the number of viable cells per field is improved. Goblet cells are mucins-secreting cells with an important role in ocular surface protection. It is therefore important that the MUC5AC secretory capacity of these cells is maintained. This was verified through MUC5AC immunohistological staining of the treated eyes (FIG. 6). Again, the Latanoprost Emulsion of the invention presented a better MUC5AC staining when compared to the other test item-treated eyes. The Latanoprost Emulsion of the invention was also able to improve the natural healing process and to control and alleviate the negative signals of uncontrolled fibrosis.

Example 2

In Vitro Experiments

Brief description of the protocol: human corneal epithelial (HCE) cells (100 000 cells per well) were plated in 6-well plates and cultured until confluence. At confluence the cell monolayer was scraped with a yellow tip, the medium removed and incubated for 30 min with 1/10 dilutions of the different test articles (PBS (phosphate buffer solution), Xalatan® (aqueous solution of latanoprost at 0.005%), 0.02% BAK (benzalkonium chloride aqueous solution), and the Latanoprost Emulsion of the invention (with 0.005% latanoprost). Following the treatment, test article dilutions were removed and replaced by fresh culture medium. The scraping closure was assessed 2 and 24 h post treatment. Immunohistology of proliferation marker (Ki67) was also performed on cells cultured for 24 h post scraping.

Results: 2 and 24 h after the scraping, pictures of the cell monolayer were taken to assess the efficacy of the different treatment on the scraping closure. Clearly, the Latanoprost Emulsion of the invention displays a positive effect on cell survival and migration (FIGS. 7 & 8). There were less dead cells, and the closure of the cleft was merely complete 24 h post scraping with the Latanoprost Emulsion of the invention, while Xalatan®, 0.02% BAK solution and even PBS displayed no or only little closure.

The compilation of these data for the different conditions in the test demonstrated that the Latanoprost Emulsion of the invention was able to increase the pace of wound closure, while both Xalatan® and 0.02% BAK solution altered the process of wound healing in vitro. No closure was observed with the latter two test items (see FIG. 9), as demonstrated by the % of wound closure 24 h post scraping that remains very low, 6% and 8% for Xalatan® and the 0.02% BAK solution, respectively. By opposition, Latanoprost Emulsion has % of wound closure of 85%. This is confirmed by immunohistology data for Ki67, a proliferation marker (see FIG. 10). More positive cells for Ki67 (i.e. dividing cells) were present close to the edge of the scraping wound in plates treated with the Latanoprost Emulsion of the invention.

This shows the healing properties of the composition of the invention on corneal cells.

Example 3

Compositions of Prostaglandin F2alpha

| Composition 1 | | |
|---|---|---|
| Ingredient | Function | % w/w |
| Travoprost | Active Ingredient | 0.002% |
| Polysorbate 80 | Wetting agent | 0.050% |
| Glycine | Osmoprotecting agent | 0.5% |

-continued

| Composition 1 | | |
|---|---|---|
| Ingredient | Function | % w/w |
| Erythritol | Osmoprotecting agent | 0.5% |
| Water for Injection | Diluent | Ad 100% |
| NaOH/HCl 0.1M | pH adjuster during manufacturing | |

Composition 1 combines 3 mechanisms of action: a prostaglandin F2alpha analogue, a wetting agent polysorbate 80, two osmoprotectants plus a hypoosmotic effect to protect corneal cells.

| Composition 2 | | |
|---|---|---|
| Ingredient | Function | % w/w |
| Acid free latanoprost | Active Ingredient | 0.0005% |
| Vitamin A | Healing agent | 0.005% |
| Glycerin | Osmotic agent | 1.6% |
| Polyvinyl alcohol | Lubricating agent | 1.0% |
| Water for Injection | Diluent | Ad 100% |
| NaOH/HCl 0.1M | pH adjuster during manufacturing | |

Composition 2 combines three mechanisms of actions: a prostaglandin F2alpha analogue, vitamin A and a lubricating agent plus a hypoosmotic effect to protect corneal cells.

| Composition 3 | | | |
|---|---|---|---|
| Phase | Ingredient | Function | % w/w |
| Oily phase | Latanoprost | Active Ingredient | 0.005% |
| | Medium-Chain Triglycerides | Oily agent | 1.00% |
| | Polysorbate 80 | Surfactant | 0.050% |
| | Cetalkonium Chloride | Cationic agent | 0.005% |
| Aqueous phase | Glycerin | Osmotic agent | 2.4% |
| | Water for Injection | Diluent | Ad 100% |
| | NaOH 0.1M | pH adjuster during manufacturing | |
| | Nitrogen | Inert gas during manufacturing | |

Composition 3 also combines several mechanisms of action: a prostaglandin F2alpha analogue, an oil to prevent water evaporation, a lubricating agent glycerol.

The invention claimed is:

1. A method for treating corneal and/or conjunctival lesions in a patient in need thereof, comprising topically administering a composition comprising a therapeutic amount of a prostaglandin F2alpha or analogue thereof, as sole active agent, wherein said analogue is selected from the group consisting of latanoprost, acid-free latanoprost, 15-ketolatanoprost, latanoprost nitroxide unoprostone, bimatoprost, travoprost and tafluprost.

2. The method according to claim 1, wherein the therapeutic amount of prostaglandin F2alpha or analogue thereof in the composition ranges from 0.0001 to 0.005% in weight to the weight of the total composition.

3. The method according to claim 1, wherein the composition is free of deleterious preservative.

4. The method according to claim 1, wherein the composition is an aqueous solution, a viscous or semi-viscous gel, a suspension, a solid insert or an anionic or cationic emulsion.

5. The method according to claim 1, wherein the composition is in the form of eye drops, artificial tears, gel or ointment.

6. The method according to claim 1, wherein the composition is isoosmotic or hypoosmotic.

7. The method according to claim 1, wherein the composition further comprises osmoprotectants, or other healing agents, buffers, thickening agents, moisturizing agents and antioxidants agents.

8. The method according to claim 1, wherein the composition is administered at least once per day, with a maximum of four instillations per day.

9. The method according to claim 1, wherein the composition is administered during three to five days.

10. The method according to claim 1, wherein the composition is unpreserved, preservative-free, self-preserved or preserved with soft preservatives.

11. The method according to claim 1, wherein the composition further comprises an anti-glaucoma agent, an anti-inflammatory agent, an antibiotic, an antiviral or an antifungal, and other secretagogue compounds.

12. The method according to claim 1, wherein the patient is affected by glaucoma and the therapeutic amount of prostaglandin F2alpha or analogue thereof in the composition is 0.004 to 0.005% in weight to the weight of the total composition.

13. The method according to claim 1, wherein the patient is not affected by glaucoma, and the therapeutic amount of prostaglandin F2alpha or analogue thereof in the composition is 0.0001% to 0.004% in weight to the weight of the total composition.

14. The method according to claim 2, wherein the composition is free of deleterious preservative.

* * * * *